United States Patent [19]
Kodama et al.

[11] Patent Number: 5,405,407
[45] Date of Patent: Apr. 11, 1995

[54] CYLINDER FOR ARTIFICIAL LEG

[75] Inventors: Yoshihiro Kodama, Kobe; Yasukazu Furuichi, Akashi, both of Japan

[73] Assignee: Nabco Limited, Kobe, Japan

[21] Appl. No.: 4,765

[22] Filed: Jan. 14, 1993

[30] Foreign Application Priority Data

Feb. 24, 1992 [JP] Japan ................... 4-073449

[51] Int. Cl.⁶ ............... A61F 2/64; A61F 2/74
[52] U.S. Cl. ................. 623/44; 92/181 P; 92/85 B; 91/22; 91/399; 188/317
[58] Field of Search ......... 623/43, 44, 39, 26; 92/181 P, 85 B; 91/399, 22; 188/317, 322.22

[56] References Cited
U.S. PATENT DOCUMENTS 5,062,857  11/1991  Berringer et al. ............... 623/25

FOREIGN PATENT DOCUMENTS 0714881  8/1965  Canada ................... 92/85 B
52-47638  12/1977  Japan .

*Primary Examiner*—David H. Willse
*Attorney, Agent, or Firm*—Wegner, Cantor, Mueller & Player

[57] ABSTRACT

In an artificial leg for a person having an upper thigh cut and a knee joint lost, a cylinder disposed between upper and lower leg members, which are coupled through a pivotable joint, for controlling bending and straightening of the joint by an air cushion for convenience of walking. The cylinder includes a cylindrical sleeve closed at both ends and a piston having a piston rod and sliding in the sleeve, and has its structure improved by using as a cushion one of two inner cavities separated by the piston, which encloses the piston rod, thereby buffering butting between the upper and lower leg members to remove unpleasant shock resulting at the end of straightening the joint.

3 Claims, 3 Drawing Sheets

CYLINDER FOR ARTIFICIAL LEG

BACKGROUND OF THE INVENTION

This invention relates to a cylinder used in an artificial leg for a person having upper thigh cut and an upper thigh stub. Typical examples of this type of artificial leg and cylinder used therein are disclosed in the Japanese patent publication No. S52-47638 and the description of prior art will be made below in connection with these examples.

As shown in FIG. 1, an artificial leg has upper and lower leg members 1 and 2 pivotably coupled through a joint 3 and a cylinder 4 is bridged therebetween at pivots 5 and 6 to support the joint of both members 1 and 2. The cylinder extends and contracts with straightening and bending of the joint caused by a walking action and serves to suitably brake and buffer the straightening and bending motion of the joint by means of internal air pressure.

As shown in FIGS. 2 and 3, the prior art cylinder comprises a cylindrical sleeve 10 having both ends closed with a head cover 12 and a rod cover 14, and a piston 16 fixed to a piston rod 18 penetrating through the rod cover 14 and fit slidably in the sleeve 10. The rod 18 has a coupling 20 to be coupled to the pivot 5 of the upper member 1 at an end thereof and the head cover 12 has a coupling 22 to be coupled to the pivot 6 of the lower member 2. The cylinder 4 may be inverted to couple the coupling 20 to the lower member 2 and the coupling 22 to the upper member 1, if the circumstances admit.

The piston 16 partitions the inner cavity of the sleeve 10 into a "head chamber" 24 adjacent to the head cover 12 and a "rod chamber" 26 adjacent to the rod cover 14. FIG. 2 shows a cylinder extended to give the maximum volume of the head chamber 24 and FIG. 3 shows the cylinder contracted to give the maximum volume of the rod chamber 26. The piston 16 has a check valve 28 for connecting the head chamber 24 with the rod chamber 26 and the check valve 28 is arranged to allow an air flow from the rod chamber 26 to the head chamber 24 but stop a backward flow. Therefore, the cylinder is subjected to large resistance to contracting less resistance to and the joint of extending the artificial leg straightens easily but bends awkwardly. As shown, the piston rod 18 includes a throttle valve 30 having a needle valve body 32 and connecting the head chamber 24 to the rod chamber 26, and the valve body 32 is moved forward and backward by an adjusting screw 34 to change the aperture of the throttle valve 30. Therefore, the contracting resistance of the cylinder or the bending resistance of the joint can be adjusted by adjusting the throttle valve 30.

As shown much better in FIG. 3, the piston rod 18 is partially enlarged in its diameter adjacent to the piston 16 and this portion will be referred to as "major diameter portion" 36. The penetration hole formed in the rod cover 14 for passing the rod 18 is partly enlarged to form a cavity 38 for receiving the major diameter portion 36 and an O-ring 40 having a V-shaped cross-section is disposed in the opening thereof. As shown in FIG. 2, the major diameter portion 36 enters the cavity 38 and forms a cushioning chamber 42 in the bottom of cavity 38 at the time of extension of the cylinder. Part of the air in the cushioning chamber 42 is discharged to the rod chamber 26 through a resistive path 44 which is schematically shown in a dashed line.

Referring next to FIG. 4 which schematically shows a human walking state, A1, A2, A3, A4, A5 and A6 denote head, back, waist, knee, heel and toe portions, respectively. While the drawing shows a cycle of walking after the heel portion A5 of one leg lands on the ground until it lands again thereon, which is decomposed into thirteen positions, in total, B1, B2, ... B7 and C1, C2, ... C6, the period from the position B1 and B7 in which the heel or toe portions A5 or A6 touches the ground is referred to as "standing phase" B and the period from the position C1 to C6 in which both heel and toe portions A5 and A6 are apart from the ground is referred to as "idling phase" C. At the time of walking, when one leg is in the standing phase B, the other leg is in the idling phase C, and the walking is effected by repeating the standing and idling phases, alternately.

At the position B1, the upper and lower leg 1 and 2 are substantially in line and the head and back portions A1 and A2 are a little behind the heel portion A5. From this position B1 to the position B4, the upper and lower leg 1 and 2 rotate about the heel portion A5 as they are in line and, at about the same time as the toe portion A6 comes in contact with the ground at the position B4, all portions from the head portion A1 to the heel portion A5 are substantially straightened into an erected state. While these portions from the head portion A1 to the heel portion A5 fall gradually forward as they are nearly in line from the erect positions B4 and the position B7, the upper part of the body begins to rise about the waist portion A3 after about the position B7, and the upper and lower leg 1 and 2 rotate before as they are before about the toe portion A6. Next, after the position C1, the toe portion A6 leaves the ground and the lower leg 2 begins to rotate in clockwise direction about the waist portion A3 with respect to the upper leg 1 or, in other words, bending of the knee A4 begins and, at the position C3, the bending becomes maximum. In contrast, from the position C3 to C6, the lower leg 2 rotates in counterclockwise direction about the waist portion A3 with respect to the upper leg 1 and, at the position C6, they reach into a nearly straightened state.

The cylinder 4 operates as follows during each cycle of walking as described above. During the standing phase B in which the upper and lower leg members 1 and 2 are nearly in line, the cylinder 4 is substantially in the extended state as shown in FIG. 2. After the position C1, however, it begins to contract and the air in the head chamber 24 flows through the throttle valve 30 into the rod chamber 26. By adjusting this air flow by the needle valve body 32, the swing-up speed of the lower leg member 2 can be adjusted adequately. At the maximum swing-up position C3 of the lower leg member 2, the cylinder 4 arrives at the contracted state as shown in FIG. 3 and the air remaining in the head chamber 24 is compressed in a depression 46 formed in the head cover 12. With a repulsive force of this compressed air, the cylinder 4 begins to extends thereafter to commence swing-down of the lower leg member 2. Then, the air in the rod chamber 26 flows through the check valve 28 into the head chamber 24 and, therefore, the lower leg member 2 is smoothly swung down. Finally, at the position C6, the lower leg members 1 and 2 are straightened completely and the cylinder 4 is in the extended state of FIG. 2, in which the major diameter portion 36 fits in the cavity 38 to form the cushioning chamber 42. The cushioning chamber 42 serves to reduce shock when the upper end 2a of the lower leg member 2 butts against the lower end 1a of the upper leg member 1.

In the above-mentioned prior art cylinder, however, the shock reducing effect of the cushioning chamber 42 is relatively small since its volume is small and the air therein is rapidly compressed. Especially, when swing-down speed of the lower leg member 2 is high, the above-mentioned shock cannot be absorbed completely and, therefore, the wearer of the prosthesis is subjected to an unpleasant feeling due to this shock when he increases his walking speed. Even if the walking speed is relatively low, there should be the same problem when the artificial leg is long and heavy.

Accordingly, an object of this invention is to provide an improved cylinder for artificial legs, which has a large cushioning chamber for completely absorbing the above-mentioned shock to enable comfortable walking regardless of the walking speed and the weight of the lower leg member.

SUMMARY OF THE INVENTION

The cylinder for artificial legs according to this invention, which can achieve the above object, has substantially the same structure as the prior art cylinder as descried above. However, its piston 116 has no check valve 28 connecting the rod chamber 126 with the head chamber 124 and, instead, the major diameter portion 136 of its position rod 118 has a path which is formed penetrating longitudinally therethrough and opening laterally at a position on the rod 118 which is adjacent to the major diamter portion 136, and a check valve is disposed in this path in the same direction as the above-mentioned check valve 28.

When the cylinder with this structure extends, the air in the rod chamber 126 flows through the check valve in the major diameter portion 136 into the head chamber 24 before the major diameter portion 136 arrives at the rod cover 114. However, after the major diameter portion 136 fits in the cavity 138 in the rod cover 114, the rod chamber 126 is completely isolated excepting the resistive path 144 to form a large cushioning chamber with itself, which can completely absorb any shock.

These and other features and operation of this invention will be described in more detail below about an embodiment thereof with reference to the accompanying drawings.

BRIEF DESCRIPTION OF THE DRAWINGS

In the drawings.

Throughout the drawings, same reference numerals or symbols are given to the same or corresponding structural components.

DESCRIPTION OF PREFERRED EMBODIMENT

Figure 5:
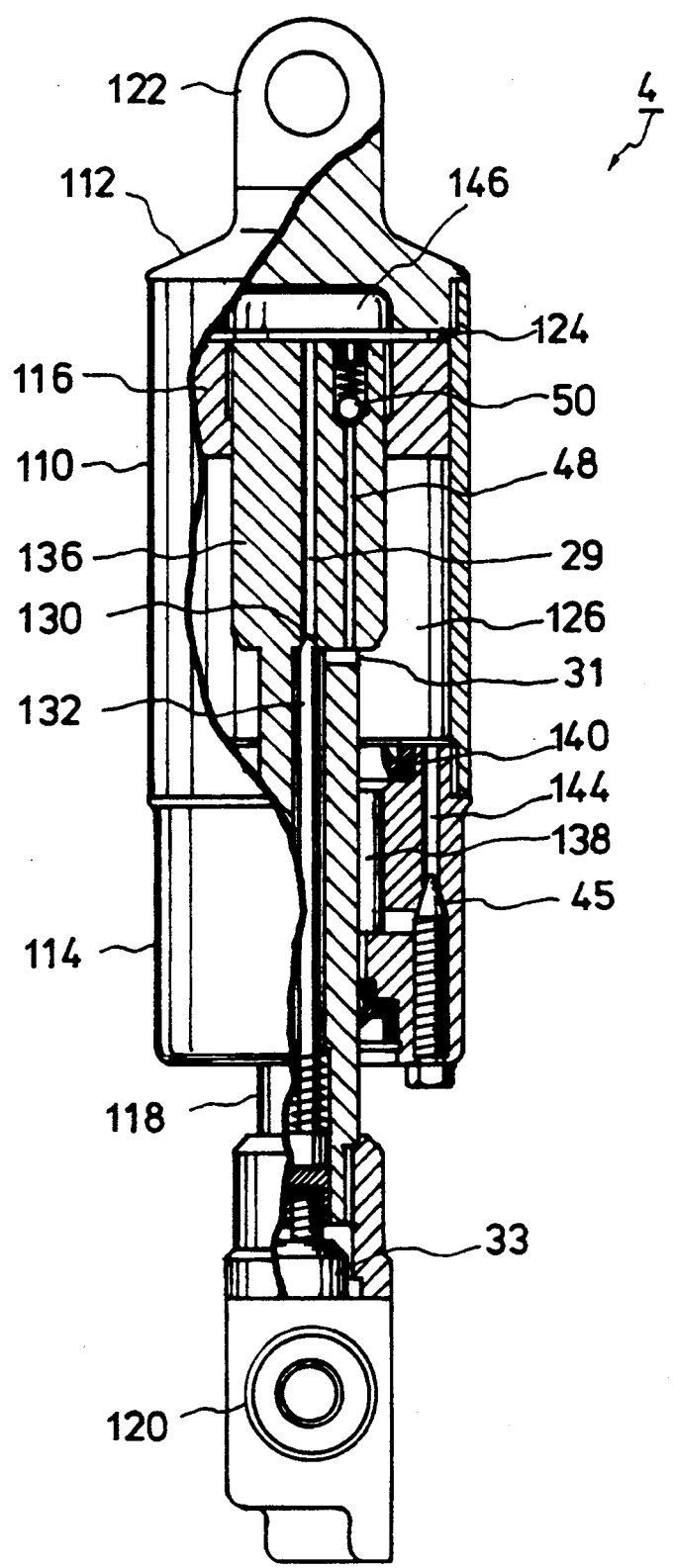
FIG. 5 is a partial longitudinal sectional view showing the contracted state of the cylinder according to this invention.

Referring to FIG. 5, as same as in the prior art, the cylinder 4 includes a cylindrical sleeve 110 having both ends closed with a head cover 112 and a rod cover 114, and a piston 116 fixed at an end of a piston rod 118 which penetrates through the rod cover 114 and slidably fits in the sleeve 110. The piston 116 partitions the inner cavity of the sleeve 110 into a head chamber 124 and a rod chamber 126 and the piston rod 118 has a major diameter portion 136 adjacent to the piston 116. The rod cover 114 has a cavity 138 for receiving the major diameter portion 136 therein and an O-ring 140 of V-shaped cross-section is disposed in the opening of the cavity 138. The rod cover 114 also has a path 144 bored therein for connecting the cavity with the rod chamber 126 and a throttle valve 45 whose aperture can be adjusted externally is disposed in the path 144. The head cover 112 has a depression 146.

The major diameter portion 136 of the piston rod 118 has a path 29 bored therein for connecting the head chamber 124 with the rod chamber 126 and a throttle valve 130 having a needle valve body 132 is disposed in the path 29. In contrast to the prior art cylinder, the path 29 does not open at the side wall of the major diameter portion 136 and it has an opening 31 in the minor diameter portion adjacent to the major diameter portion 136 as shown. The aperture of the throttle valve 130 is controlled by a motor 33 coupled to the other end of the needle valve body 132 and controlled by an electronic computer (not shown).

The major diameter portion 136 of the piston rod 118 has a second path 48 bored therein for connecting the head chamber 124 with the rod chamber 126 and a check valve 50 openable toward the head chamber 124 is disposed in the path 48. The path 48 has the opening 31 common to the path 29 in the rod chamber 126.

Figure 1:
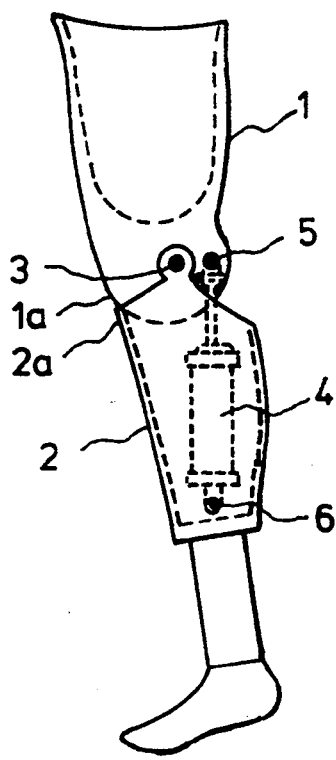
FIG. 1 is a schematic diagram showing an artificial leg in which the inventive cylinder is to be used.
Figure 4:
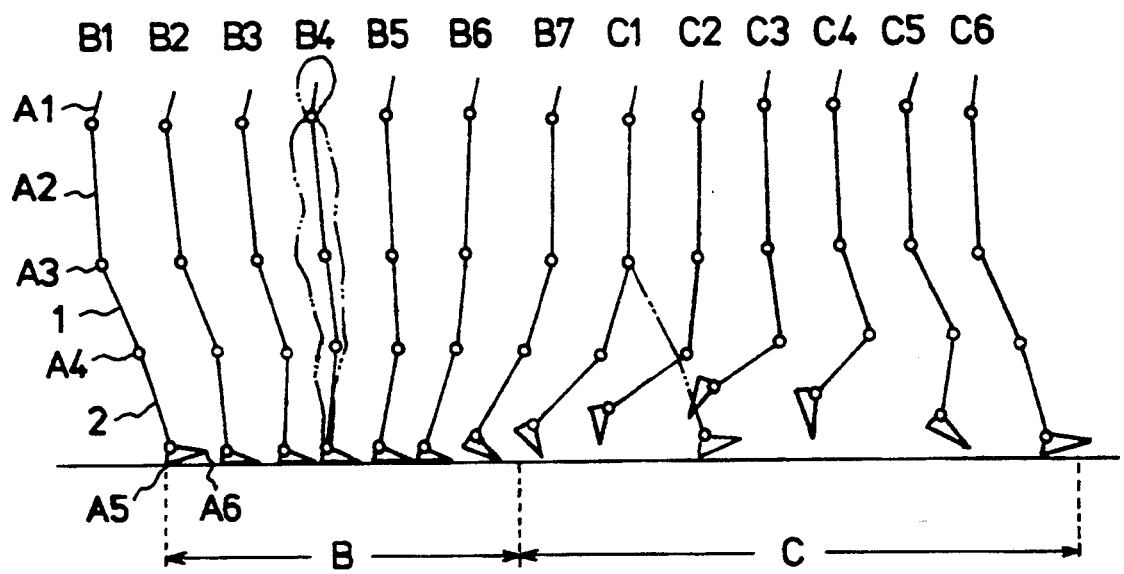
FIG. 4 is a schematic diagram illustrating a walking motion of a man.

When the cylinder 4 extends from the position as shown, the air in the rod chamber 126 flows mainly through the path 48, and the check valve 50 into the head chamber 124 and the extending motion is easily advanced. Therefore, the swing-down motion of the lower leg member 2 after the position C3 of FIG. 4 is effected also easily. When the major diameter portion 136 enters the cavity 138 in the vicinity of the position C5, however, the path 48 is shut off from the rod chamber 126 and connected to the cavity 138 instead. Therefore, the air flow from the rod chamber 126 to the head chamber 124 has no way other than passing through path 144, having the throttle valve 45 into the cavity 138 though the air in the cavity 138 easily flows through the check valve 50 to the head chamber 124. Accordingly, this air flow is subjected to the resistance of the throttle valve 45 and the extending motion is braked. Moreover, since the remaining volume of the rod chamber 126 is large enough, the braking action is relatively slow and the shock is absorbed sufficiently. This shock absorption can be freely adjusted by adjusting the throttle valve 45 in accordance with the weight of the artificial leg and also controlled by controlling the throttle valve 130. Therefore, it becomes possible to absorb the shock in conformity with the walking speed, if the walking speed is sensed and input to the computer for controlling the motor 33. Furthermore, if the motor 33 is controlled to close the throttle valve 130 at this extended position of the cylinder, the air pressure in the head chamber 124 is sufficient for holding the upper and lower leg members 1 and 2 in a nearly straightened state during the standing phase B from the position B1 to B7.

When the cylinder 4 contracts succeedingly, the air in the head chamber 124 is compressed and part thereof flows in the cavity 138 through the throttle valve 130 since the check valve 50 is closed. Then, the air flowing into the cavity 138 pushes aside the inner periphery of the V-shaped O-ring 140 and flows into the rod chamber 26, since the volumetric change of the rod chamber 126 is much greater than that of the cavity 138. After the major diameter portion 136 of the rod 118 comes out of the cavity 138, the air flow passing the throttle valve 130 flows directly into the rod chamber 126. If the computer for the motor 33 is preset to open the throttle valve 130 in the contracting process of the cylinder, the swing-up (bending) motion of the lower thigh member 2 after the position C1 is effected easily and naturally.

Figure 2:
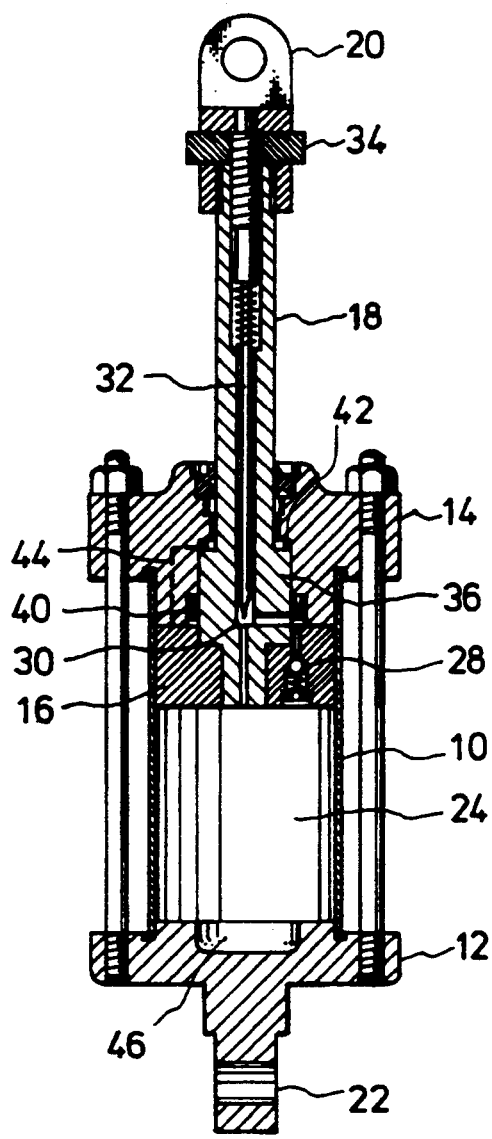
FIG. 2 is a longitudinal sectional view showing the stretched state of the prior art cylinder which is the start point of this invention.
Figure 3:
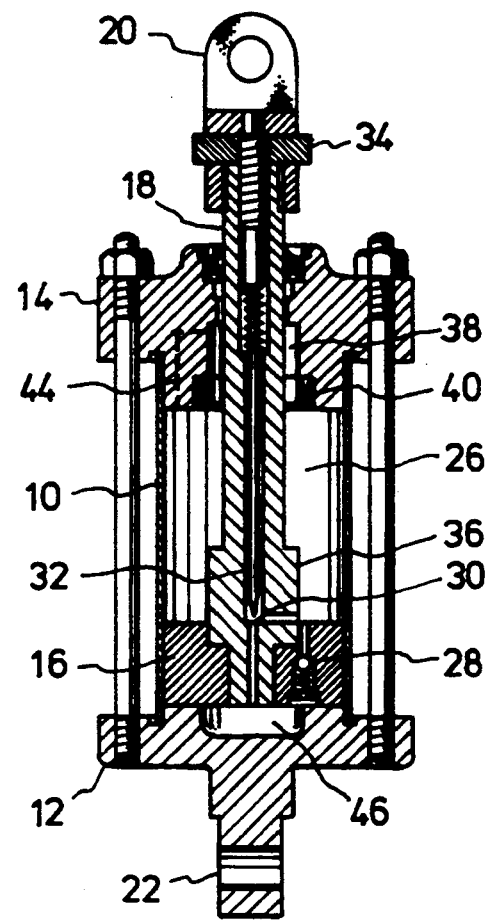
FIG. 3 is a longitudinal sectional view showing the contracted state of the cylinder of FIG. 2.

It should be noted that the above description has been made for the illustrative purpose only and odes not mean any limitation of the invention. It is obvious to those skilled in the art that various variations and modifications can be made on the above embodiment within the scope of this invention as defined in the appended claims. For example, the needle valve body 132 may be adjusted manually as shown in FIGS. 2 and 3 instead of using the motor 33.

We claim:

1. In a cylinder for an artificial leg including upper and lower leg members pivotally coupled with each other, said cylinder for bridging between said upper and lower leg members for providing suitable resistance to bending and unbending motions of said leg, and having:
   a cylindrical sleeve having each end closed with a rod cover and a head cover, respectively;
   a piston assembly having a piston fixed to an end of a piston rod penetrating through said rod cover and slidably fitting in said sleeve, said piston partitioning an interior of said sleeve into a rod chamber adjacent to said rod cover and a head chamber adjacent to said head cover;
   a major diameter portion of said piston rod bending situated between said piston and a remaining minor diameter portion of said piston rod;
   a cylindrical cavity formed in said rod cover for receiving said major diameter portion therein during extending of said piston rod from said cylinder,
   a first fluid flow path, formed in said rod cover, provided with an adjustable first throttle valve and connecting said cavity with said rod chamber;
   second and third fluid flow paths, formed in said piston assembly, connecting said head chamber with said rod chamber, the improvement comprising:
   said second and third paths being provided with an opening, on a rod chamber side of said piston, through said minor diameter portion of said piston rod and adjacent to said major diameter portion such that direct fluid flow from said rod chamber is restricted to and by said first path during said receiving of said major diameter portion in said cavity when extending said piston rod and thus unpleasant shock to a wearer of said artificial leg is prevented during said extending.

2. The improvement as set forth in claim 1, and further comprising:
   said major diameter portion being sufficient to fit loosely in an opening of said cylindrical cavity;
   O-ring means, situated in said opening, for contacting said major diameter portion when said major diameter portion enters said cavity and allowing fluid flow therepast from said cavity to said rod chamber while stopping any backward fluid flow therepast from said rod chamber to said cavity.

3. The improvement as set forth in claim 1, and further comprising:
   an adjustable second throttle valve provided in at least one of said second and third fluid flow paths; and
   motor means for adjusting said second throttle valve according to control by an electronic computer.

* * * * *